(12) United States Patent
Nakamura et al.

(10) Patent No.: US 9,096,538 B2
(45) Date of Patent: Aug. 4, 2015

(54) PHARMACEUTICAL COMPRISING PPAR AGONIST

(75) Inventors: Yoshikuni Nakamura, Kobe (JP); Ikuko Hanano, Kobe (JP); Jun Inoue, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 854 days.

(21) Appl. No.: 13/406,990

(22) Filed: Feb. 28, 2012

(65) Prior Publication Data

US 2012/0220612 A1 Aug. 30, 2012

Related U.S. Application Data

(62) Division of application No. 12/085,548, filed as application No. PCT/JP2006/323601 on Nov. 27, 2006, now Pat. No. 8,148,389.

(30) Foreign Application Priority Data

Nov. 28, 2005 (JP) ................................. 2005-342025

(51) Int. Cl.

| | | |
|---|---|---|
| *A61K 31/216* | (2006.01) | |
| *A61K 31/192* | (2006.01) | |
| *C07D 239/47* | (2006.01) | |
| *A61K 31/426* | (2006.01) | |
| *A61K 31/505* | (2006.01) | |
| *C07D 277/26* | (2006.01) | |

(52) U.S. Cl.
CPC ............ *C07D 239/47* (2013.01); *A61K 31/216* (2013.01); *A61K 31/426* (2013.01); *A61K 31/505* (2013.01); *C07D 277/26* (2013.01)

(58) Field of Classification Search
None
See application file for complete search history.

(56) References Cited

U.S. PATENT DOCUMENTS

| | | | |
|---|---|---|---|
| 6,242,196 B1 | 6/2001 | Spiegelman et al. | |
| 6,706,746 B2 | 3/2004 | Fujita et al. | |
| 7,358,255 B2 | 4/2008 | Nakamura et al. | |
| 2002/0187926 A1 | 12/2002 | Knudsen et al. | |
| 2004/0076695 A1* | 4/2004 | Gilbard ........................ | 424/765 |
| 2007/0149580 A1* | 6/2007 | Chandross et al. ........... | 514/365 |

FOREIGN PATENT DOCUMENTS

| | | |
|---|---|---|
| JP | 2001-39976 | 2/2001 |
| JP | 2005-8570 | 1/2005 |
| WO | 98/25598 | 6/1998 |
| WO | 00/71540 | 11/2000 |
| WO | 02/069994 | 9/2002 |
| WO | 02/076177 | 10/2002 |
| WO | 2005/039574 | 5/2005 |

OTHER PUBLICATIONS

T. M. Willson et al.,"ThePPAR:s: From Orphan Receptors to Drug Discovery", J. Med. Chem., vol. 43, No. 3, pp. 527-550, Feb. 24, 2000.
A. Bonazzi et al., "Regulation of Cyclooxygenase-2 by Hypoxia and Peroxisome Proliferators in the Corneal Epithelium", The Journal of Biological Chemistry, vol. 275, No. 4, pp. 2837-2844, Jan. 28, 2000.
M. Kim et al., "Limited Cooperation Between Peroxisome Proliferator-Activated Receptors and Retinoid X Receptor Agonists in Sebocyte Growth and Development", Molecular Genetics and Metabolism, vol. 74, pp. 362-369, 2001.
N. S. Tan et al., "Peroxisome Proliferator-Activated Receptor (PPAR)-β as a Target for Wound Healing Drugs", Am. J. Clin. Dermatol., vol. 4, No. 8, pp. 523-530, 2003.
M. Laniado-Schwartzman et al., Invest. Ophthalmol. Vis. Sci., vol. 41, No. 4, S905, 4815-B762, Mar. 15, 2000.
Supplementary European Search Report issued Jul. 6, 2010 in corresponding European Application EP 06 83 3405.
M.L. Sznaidman et al., "Novel selective small molecule agonists for peroxisome proliferator-activated receptor delta (PPAR delta)-synthesis and biological activity", Bioorganic & Medicinal Chemistry Letters, vol. 13, No. 9, p. 1517-1521, May 5, 2003, XP002995419, ISSN: 0960-894X.
R.L. Rosenfield et al., "Mechanisms of androgen induction of sebocyte differentiation", Dermatology, vol. 196, No. 1, p. 43-46, Jan. 1, 1998, XP009074036, ISSN: 1018-8665.
Dressel et al. (The Peroxisome Proliferator-Activated Receptor β/Agonist, GW501516, Regulates the Expression of Genes Involved in Lipid Catabolism and Energy Uncoupling in Skeletal Muscle Cells, Molecular Endocrinology, 2003, 17(12):2477-2493 (U.S. Appl. No. 12/085,548).
Gilde AJ et al. Peroxisome proliferator-activated receptor (PPAR) α and PPARβ/δ but not PPARγ, modulate the expression of genes involved in cardiac lipid metabolism. Circ Res. Mar. 21, 2003;92(5):518-24.
Chinese Office Action (together with English translation) issued Mar. 8, 2010 in corresponding Chinese Patent Application No. 200680051899.3.
Kim DJ et al., PPARbeta/delta selectively induces differentiation and inhibits cell proliferation. Cell Death Differ. Jan. 2006;13(1):53-60.

* cited by examiner

*Primary Examiner* — Bong-Sook Baek
(74) *Attorney, Agent, or Firm* — Wenderoth, Lind & Ponack, L.L.P.

(57) ABSTRACT

An object of the present invention is to provide an agent for promoting proliferation of a meibomian gland epithelial cell and a corneal epithelial cell, as well as provide an agent for treating an ocular disease such as meibomian gland dysfunction or evaporative dry eye.
There are provided an agent for promoting proliferation of a meibomian gland epithelial cell or a corneal epithelial cell, containing a PPARα or δ agonist as an active ingredient, as well as an agent for treating an ocular disease such as meibomian gland dysfunction or evaporative dry eye, containing a PPARα or δ agonist as an active ingredient.

4 Claims, 1 Drawing Sheet

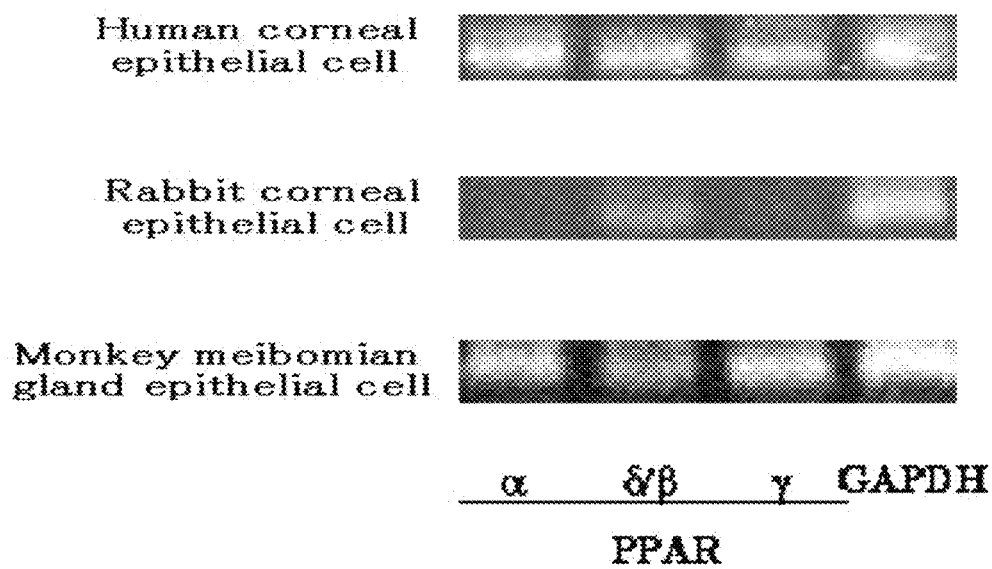

PHARMACEUTICAL COMPRISING PPAR AGONIST

This application is a Divisional of U.S. application Ser. No. 12/085,548, filed May 27, 2008, which is a national stage of International Application No. PCT/JP2006/323601 now U.S. Pat. No. 8,148,389 filed Nov. 27, 2006.

TECHNICAL FIELD

The present invention relates to an agent for promoting proliferation of a meibomian gland epithelial cell or a corneal epithelial cell, comprising a PPAR (Peroxisome Proliferator Activated Receptor) α or δ agonist as an active ingredient.

BACKGROUND ART

A meibomian gland is a lipid-producing gland included in the upper and lower eyelids, and secretes a lipid through an opening situated on a conjunctival side from eyelashes of eyelids. A lipid layer constituting a tear fluid contains a lipid supplied from the meibomian gland as a component, and prevents the tear fluid from evaporating from an eye surface. It is known that, in a meibomian gland dysfunction or meibomitis patient, the function of the meibomian gland is deteriorated, and a secretion amount of a lipid is decreased, causing hyperevaporative dry eye, a keratoconjunctival epithelial disorder, corneal epithelial erosion and corneal ulcer, which are associated with dry eye, and the like.

In addition, a cornea consists of an ectodermal epithelium and a mesodermal anterior limiting layer (Bowman's membrane)/stroma/posterior limiting layer (Descemet's membrane)/endothelium. Since the cornea is the frontmost part of eyeballs, it easily undergoes the influence of the external environment and, as a result, various disorders are generated. Examples of a disease associated with a damage or a defect of a corneal epithelial cell include dry eye syndrome, corneal ulcer, superficial punctate keratitis, corneal epithelial erosion, ocular allergic diseases associated with a corneal lesion such as spring catarrh and atopic keratoconjunctivitis, and the like.

On the other hand, PPAR is one of intranuclear receptors, which is expressed in almost all vertebrates, and is said to be a transcription factor group closely involved in intracellular saccharide-lipid metabolism and differentiation of a cell. As a subtype, α, δ and γ are known. A PPARδ is termed as PPARβ in some cases (Non-Patent Literature 1).

As the distribution of PPAR in an ocular tissue, it is known that PPARα and β are expressed in a corneal epithelial cell of a rabbit (Non-Patent Literature 2).

Previously, it has been reported that 5-[4-(6-methoxy-1-methyl-1H-benzimidazol-2-ylmethoxy)benzyl]thiazolidine-2,4-dione having a PPAR activating action can be utilized as an agent for treating a keratoconjunctival disorder (Patent Literatures 1 and 2), and a PPARα, δ or γ agonist is administered in treating an ocular disease (conjunctivitis, dry eye syndrome, corneitis, or the like) (Patent Literature 3). In addition, PPARα is known to be distributed in the liver, kidney and the like and to act on lipid metabolism/transportation and, further, it has been reported that an agonist thereof can be utilized as an agent for treating a corneal disease (Patent Literature 4). With respect to a PPARδ agonist, it has previously been reported that the agonist promotes proliferation and differentiation of a rat sebaceous gland epithelial cell (Non-Patent Literature 3), and promotes healing of skin injury (Non-Patent Literature 4). Additionally, a method of stimulating proliferation of a β-cell by administering a non-thiazolidinedione PPAR ligand and a GLP-1 derivative (Patent Literature 5), and inhibition of proliferation of a leukemia cell and a prostate cancer cell by pioglitazone which is a PPARγ agonist (Patent Literature 6) are known.

However, the expression and function of PPARα, δ and γ in each animal species and each tissue or cell contain many questions to be answered, and which PPAR agonist is useful for human ocular diseases is not known.

[Patent Literature 1] WO 2005/039574
[Patent Literature 2] Japanese Patent Application Laid-Open (JP-A) No. 2001-39976
[Patent Literature 3] WO 2002/076177
[Patent Literature 4] JP-A No. 2005-008570
[Patent Literature 5] WO 2002/69994
[Patent Literature 6] WO 1998/25598
[Non-Patent Literature 1] J Med Chem 2000, 43: 527-550
[Non-Patent Literature 2] J Biol Chem 2000, 275: 2837
[Non-Patent Literature 3] Molecular Genetic and Metabolism 2001, 74: 362-369
[Non-Patent Literature 4] Am J Clin Dermatol 2003, 4 (8): 523-530

DISCLOSURE OF THE INVENTION

Problems to be Solved by the Invention

An object of the present invention is to provide an agent capable of promoting proliferation of a meibomian gland epithelial cell and a corneal epithelial cell, which can be a fundamental treatment of ocular diseases such as dry eye and the like, as well as a therapeutic agent for ocular diseases such as meibomian gland dysfunction, hyperevaporative dry eye and the like, which contains said promoting agent.

Means for Achieving the Object

In view of the aforementioned problems, the present inventors conducted various investigations and as a result, found out that a PPARα or δ agonist has an activity of promoting proliferation of a meibomian gland epithelial cell and a corneal epithelial cell, resulting in completion of the present invention.

Accordingly, the present invention includes at least the following contents.

(1) An agent for promoting proliferation of a meibomian gland epithelial cell, comprising a PPARα or δ agonist as an active ingredient.
(2) An agent for promoting proliferation of a corneal epithelial cell, comprising a PPARα or δ agonist as an active ingredient.
(3) An agent for treating meibomian gland dysfunction, comprising a PPARα or δ agonist as an active ingredient.
(4) An agent for treating a corneal epithelial disorder, comprising a PPARα or δ agonist as an active ingredient.
(5) An agent for treating hyperevaporative dry eye, comprising a PPARα or δ agonist as an active ingredient.
(6) An agent for promoting proliferation of a meibomian gland epithelial cell, comprising a PPARδ agonist as an active ingredient.
(7) An agent for promoting proliferation of a corneal epithelial cell, comprising a PPARδ agonist as an active ingredient.
(8) An agent for treating meibomian gland dysfunction, comprising a PPARδ agonist as an active ingredient.
(9) An agent for treating a corneal epithelial disorder, comprising a PPARδ agonist as an active ingredient.
(10) An agent for treating hyperevaporative dry eye, comprising a PPARδ agonist as an active ingredient.

(11) The agent according to any one of (1) to (5), wherein the PPARα or δ agonist is a compound represented by the formula (I):

[Chemical formula 1]

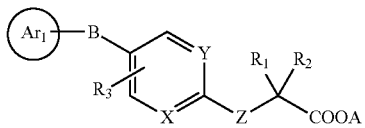

wherein
A is a hydrogen atom or an alkyl group having a carbon number of 1 to 6,
B is a linker selected from the group consisting of —CO—, —NH—, —(CH$_2$)$_n$—S—, —(CH$_2$)$_n$—O— and —O—(CH$_2$)$_n$—O— wherein n is an integer of 1 to 3,
X and Y are the same or different, and each is a carbon atom or a nitrogen atom,
Z is an oxygen atom, a sulfur atom or —CH$_2$—,
Ar$_1$ is a 5- to 6-membered aromatic cyclic group optionally having 1 to 3 substituents,
R$_1$ and R$_2$ are the same or different and each is a hydrogen atom or an alkyl group having a carbon number of 1 to 6, and
R$_3$ is hydrogen, a halogen atom or an alkyl group having a carbon number of 1 to 6,
or a pharmacologically acceptable salt thereof.

(12) The agent according to any one of (6) to (10), wherein the PPARδ agonist is a compound represented by the formula (II):

[Chemical formula 2]

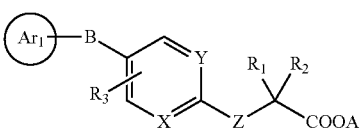

wherein
A is a hydrogen atom or an alkyl group having a carbon number of 1 to 6,
B is a linker selected from the group consisting of —(CH$_2$)$_n$—S— and —O—(CH$_2$)$_n$—O— wherein n is an integer of 1 to 3,
X and Y are the same or different, and each is a carbon atom or a nitrogen atom,
Z is an oxygen atom, a sulfur atom or —CH$_2$—,
Ar$_1$ is a 5- to 6-membered aromatic cyclic group optionally having 1 to 3 substituents,
R$_1$ and R$_2$ are the same or different, and each is a hydrogen atom or an alkyl group having a carbon number of 1 to 6, and
R$_3$ is hydrogen, a halogen atom or an alkyl group having a carbon number of 1 to 6
or a pharmacologically acceptable salt thereof.

(13) The agent according to (11) or (12), wherein the PPARδ agonist is (4-(3-(4-acetyl-3-hydroxy-2-propyl)phenoxy) propoxyphenoxy)acetic acid, (2-methyl-4-(((4-methyl-2-(4-(trifluoromethyl)phenyl)-5-thiazolyl)methyl)thio)phenoxy)acetic acid or (4-(((2-(3-fluoro-(4-(trifluoromethyl) phenyl)-4-methyl-5-thiazolyl)methyl)thio)-2-methylphenoxy)acetic acid, or a pharmacologically acceptable salt thereof.

(14) The agent according to (11), wherein the PPARα agonist is 1-methylethyl 2-(4-(4-chlorobenzoyl)phenoxy)-2-methylpropionate or ((4-chloro-6-((2,3-dimethylphenyl)amino)-2-pyrimidinyl)thio)acetic acid, or a pharmacologically acceptable salt thereof.

(15) Use of a PPARα or δ agonist for production of an agent for promoting proliferation of a meibomian gland epithelial cell.

(16) Use of a PPARα or δ agonist for production of an agent for promoting proliferation of a corneal epithelial cell.

(17) Use of a PPARα or δ agonist for production of an agent for treating meibomian gland dysfunction.

(18) Use of a PPARα or δ agonist for production of an agent for treating a corneal epithelial disorder.

(19) Use of a PPARα or δ agonist for production of an agent for treating hyperevaporative dry eye.

(20) Use of a PPARδ agonist for production of an agent for promoting proliferation of a meibomian gland epithelial cell.

(21) Use of a PPARδ agonist for production of an agent for promoting proliferation of a corneal epithelial cell.

(22) Use of a PPARδ agonist for production of an agent for treating meibomian gland dysfunction.

(23) Use of a PPARδ agonist for production of an agent for treating a corneal epithelial disorder.

(24) Use of a PPARδ agonist for production of an agent for treating hyperevaporative dry eye.

(25) A method of promoting proliferation of a meibomian gland epithelial cell, comprising administering an effective amount of a PPARα or δ agonist to a subject in need of promotion of proliferation of a meibomian gland epithelial cell.

(26) A method of promoting proliferation of a corneal epithelial cell, comprising administering an effective amount of a PPARα or δ agonist to a subject in need of promotion of proliferation of a corneal epithelial cell.

(27) The method according to (25), which is performed for treating meibomian gland dysfunction.

(28) The method according to (26), which is performed for treating a corneal epithelial disorder.

(29) A method of treating hyperevaporative dry eye, comprising administering an effective amount of a PPARα or δ agonist to a patient suffering from hyperevaporative dry eye.

(30) A method of promoting proliferation of a meibomian gland epithelial cell, comprising administering an effective amount of a PPARδ agonist to a subject in need of promotion of proliferation of a meibomian gland epithelial cell.

(31) A method of promoting proliferation of a corneal epithelial cell, comprising administering an effective amount of a PPARδ agonist to a subject in need of promotion of proliferation of a corneal epithelial cell.

(32) The method according to (30), which is performed for treating meibomian gland dysfunction.

(33) The method according to (31), which is preformed for treating a corneal epithelial disorder.

(34) A method of treating hyperevaporative dry eye, comprising administering an effective amount of a PPARδ agonist to a patient suffering from hyperevaporative dry eye.

Effect of the Invention

According to the present invention, a novel agent for promoting proliferation of a meibomian gland epithelial cell or a novel agent for promoting proliferation of a corneal epithelial cell is provided, and the promoting agent promotes proliferation of a meibomian grand epithelial cell and a corneal epithelial cell. In addition, the therapeutic agent of the present invention can be effectively used for treating or improving diseases such as meibomian gland dysfunction, corneal epithelial disorder, and hyperevaporative dry eye.

BRIEF DESCRIPTION OF THE DRAWING

FIG. 1 shows expression of mRNA of PPARα, δ or γ in a cultured human corneal epithelial cell (upper column), a cultured rabbit corneal epithelial cell (middle column), and a cultured monkey meibomian gland epithelial cell (lower column).

BEST MODE FOR CARRYING OUT THE INVENTION

The present invention provides an agent for promoting proliferation of a meibomian gland epithelial cell, comprising a PPARα or δ agonist as an active ingredient. The promoting agent promotes proliferation of a meibomian gland epithelial cell. Also, the present invention provides an agent for promoting proliferation of a corneal epithelial cell comprising a PPARα or δ agonist as an active ingredient. The promoting agent promotes proliferation of a corneal epithelial cell. In the present invention, the agent for promoting cell proliferation means both of an agent having an action of promoting cell division to increase the number of cells, and an agent having an action of inhibiting cell death to increase the number of cells.

The promoting agent of the present invention comprises a PPARα or δ agonist as an active ingredient. The PPARα agonist refers to a substance having an action of binding to and activating PPARα. In addition, the PPARδ agonist refers to a substance having an action of binding to and activating PPARδ.

As the PPARα or δ agonist, various known PPARα or δ agonists can be mentioned. Specific examples of the PPARα or δ agonist include the substances described in, for example, WO2001/00603, WO99/62872, WO2002/100813, WO97/28149, WO2004/022551, WO2001/79197, WO2003/099793, WO2005/105736, WO2005/105726, WO2005/085235, WO2005/113600, WO2005/105754, WO2005/049606, WO2004/111020, WO2006/055187, WO2006/084176, WO2005/060958, WO2005/097786, WO2004/092117, WO2005/037763, WO2005/030694, WO2005/016335, WO2003/074495, WO2004/058174, JP2003-171275A, JP2005-179281A, WO2006/031969, WO2005/097763, WO2004/063165, WO2002/050048, WO2005/090966, WO2003/099793, WO2002/076959, WO2002/053547, WO2001/00603, WO97/28149, WO2004/063184, WO2006/090920, WO2006/059744, WO2006/041197, WO2003/033493, WO2003/016291, WO2002/076957, WO2002/046176, WO2002/046154, WO2002/014291, WO2001/079197, etc., and the like.

Specific examples of the PPARα or δ agonist compound include 1-methylethyl 2-(4-(4-chlorobenzoyl)phenoxy)-2-methylpropionate (fenofibrate; CAS registered No. 49562-28-9), ((4-chloro-6-((2,3-dimethylphenyl)amino)-2-pyrimidinyl)thio)acetic acid (WY-14643; CAS registered No. 50892-23-4), (4-(3-(4-acetyl-3-hydroxy-2-propyl)phenoxy)propoxyphenoxy)acetic acid (L-165041; CAS registered No. 79558-09-1), (2-methyl-4-(((4-methyl-2-(4-(trifluoromethyl)phenyl)-5-(thiazolyl)methyl)thio)phenoxy)acetic acid (GW-501516; CAS registered No. 317318-70-0), (4-(((2-(3-fluoro-4-(trifluoromethyl)phenyl)-4-methyl-5-thiazolyl)methyl)thio)-2-methylphenoxy)acetic acid (GW-0742; CAS registered No. 317318-84-6), 2-methyl-4-((2R)-2-(3-methyl-5-(4-(trifluoromethyl)phenyl)-2-thienyl)propoxy)-benzenepropionic acid (CAS registered No. 728038-95-7), 2-ethyl-2-(4-(4-(4-(4-methoxyphenyl)-piperazin-1-yl)-2-(4-trifluoromethyl-phenyl)-thiazol-5-ylmethylsulfanyl)-phenoxy)butyric acid (GSK-677954; CAS registered No. 884324-15-6), (4-(3-(3-phenyl-7-propyl-benzofuran-6-yloxy)-propylsulfanyl)-phenyl)acetic acid (L-796449; CAS registered No. 194608-80-5), and 2-(4-(3-(1-(2-(2-chloro-6-fluoro-phenyl)-ethyl)-3-(2,3-dichloro-phenyl)-ureido)-propyl)-phenoxy)-2-methylpropionic acid (GW-2433; CAS registered No. 227941-61-9).

In the present invention, further, substances (compounds) which activate PPARα or δ may be obtained by screening from a group of substances which have not been known to be PPARα or δ agonists, and such substance (compound) may be used as an active ingredient of the present invention. The PPARα or δ agonist is known to bind to a ligand binding domain (LBD) of PPARα or δ, respectively, to activate the receptor, and regulate transcription of a PPAR target gene. For utilizing this property and, at the same time, excluding the influence of other nuclear receptors present in a mammalian cell, a novel PPARα or δ agonist can be selected by a screening method using a chimeric receptor of LBD and yeast GAL4, and a reporter gene.

As the screening method, there is exemplified the PPAR-GAL4 assay (reference literature, T. M. Willson et al., Journal of Medicinal Chemistry, 2000, vol. 43, No. 4, p. 528-550 and J. M. Lehmann et al., The Journal of Biological Chemistry, 1995, vol. 270, No. 22, p. 12953-12956). Specifically, examples include a method comprising:

(a) a step of introducing, into a cell, a vector for expressing a fused protein of a DNA binding domain (DBD) of yeast transcription factor GAL4 and LBD of PPARα or δ, and a reporter plasmid containing a DNA binding element of GAL4 and a reporter gene, (b) a step of contacting the cell and a test substance, measuring an expression amount of the reporter gene in the cell, and comparing the expression amount with an expression amount in a control cell which is not contacted with the test substance, and (c) a step of selecting a substance which activates PPARα or δ based on the comparison result of (b).

In the step (a) in the aforementioned method, a cell used is a cell which does not internally express GAL4, preferably a mammalian cell. The reporter gene may be a gene which encodes a detectable protein or enzyme, and examples thereof include a LUC (luciferase) gene, a SPAP (secreted placental alkaline phosphatase) gene, a CAT (chloramphenicol acetyl transferase) gene and the like.

Preparation of the fused protein expression vector and the reporter plasmid, as well as introduction of the vector and the plasmid into a cell can be performed by the method of the aforementioned reference literature or the method known per se.

In the step (b) of the aforementioned method, the test substance may be any known compound or a novel compound, and examples thereof include a nucleic acid, a saccharide, a lipid, a protein, a peptide, an organic low-molecular compound, a compound library prepared using the combinatorial chemistry technique, a random peptide library prepared by a solid phase synthesis method or a phage display method, and natural components derived from microorganisms, animals and plants, marine organisms or the like.

In addition, in the step (b), the transcription activity of PPARα or δ due to the presence or absence of the test substance is investigated by a so-called reporter assay. The reporter assay can be performed by the method known per se depending on the reporter gene used.

In the step (c) of the aforementioned method, when the reporter activity in the presence of the test substance is significantly higher than the reporter activity in the absence thereof, the test substance can be determined to be a compound having the PPARα or δ agonist activity.

The activity of the PPARα agonist used in the present invention to a human PPARα is not more than 50 μM, preferably not more than 10 μM, further preferably not more than 5 μM as expressed by an $EC_{50}$ value. The activity of the PPARδ agonist used in the present invention to a human PPARδ is not more than 10 μM, preferably not more than 1 μM, further preferably not more than 0.1 μM as expressed by an $EC_{50}$ value. The $EC_{50}$ value is a value measured by a PPAR-GAL4 assay using human PPARα or δ (see T. M. Willson et al., Journal of Medicinal Chemistry, 2000, vol. 43, No. 4, p. 527-550).

Preferable examples of the PPARα or δ agonist include a compound having a structure represented by the following formula (I):

[Chemical formula 3]

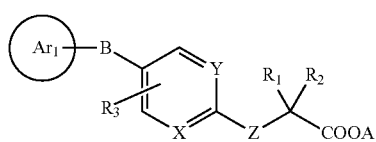

(I)

wherein
A is a hydrogen atom, an alkyl group having a carbon number of 1-6,
B is a linker selected from the group consisting of —CO—, —NH—, —(CH$_2$)$_n$—S—, —(CH$_2$)$_n$—O— and —O—(CH$_2$)$_n$—O— wherein n is an integer of 1-3,
X and Y are the same or different and each is a carbon atom or a nitrogen atom,
Z is an oxygen atom, a sulfur atom or —CH$_2$—,
Ar$_1$ is a 5- or 6-membered aromatic ring group optionally having 1-3 substituents,
R$_1$ and R$_2$ are the same or different and each is a hydrogen atom or an alkyl group having a carbon number of 1-6, and
R$_3$ is hydrogen, a halogen atom or an alkyl group having a carbon number of 1-6, or a pharmacologically acceptable salt thereof.

In the above-mentioned formula (I), examples of the "alkyl group having a carbon number of 1-6" for A include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl and the like. The alkyl group having a carbon number of 1-6 is preferably isopropyl.

In the above-mentioned formula (I), the linker for B is preferably —CO—, —NH—, —CH$_2$—S— or —O—(CH$_2$)$_3$—O—, more preferably —CH$_2$—S— or —O—(CH$_2$)$_3$—O—.

Examples of the 5- or 6-membered aromatic ring group for Ar$_1$ in the above-mentioned formula (I) include phenyl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like. The aromatic ring group is preferably phenyl or thiazolyl.

Examples of the substituent Ar$_1$ may have in the above-mentioned formula (I) include a halogen atom, a hydroxy group, an alkyl group having a carbon number of 1-6, a haloalkyl group having a carbon number of 1-6, an acyl group having a carbon number of 2-7 and a phenyl group optionally having an alkyl group having a carbon number of 1-6 or a haloalkyl group having a carbon number of 1-6. Preferable substituents are a chlorine atom, a hydroxy group, a methyl group, an acetyl group, a 4-trifluoromethylphenyl group and a 3-fluoro-4-methylphenyl group.

Examples of the "alkyl group having a carbon number of 1-6" for R$_1$ or R$_2$ in the above-mentioned formula (I) include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl and the like. The alkyl group having a carbon number of 1-6 is preferably methyl.

Examples of the "halogen atom" for R$_3$ in the above-mentioned formula (I) include a fluorine atom, a chlorine atom, a bromine atom and the like. The halogen atom is preferably a chlorine atom.

Examples of the "alkyl group having a carbon number of 1-6" for R$_3$ in the above-mentioned formula (I) include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl and the like. The alkyl group having a carbon number of 1-6 is preferably methyl.

Examples of the pharmaceutically acceptable salt of a compound represented by the formula (I) include acid addition salts with mineral acids such as hydrochloric acid, hydrobromic acid, hydroiodic acid, sulfuric acid, nitric acid, phosphoric acid and the like; organic acids such as formic acid, acetic acid, propionic acid, oxalic acid, malonic acid, succinic acid, fumaric acid, maleic acid, malic acid, tartaric acid, methanesulfonic acid, ethanesulfonic acid and the like; acidic amino acids such as aspartic acid, glutamic acid, etc., and the like. These salts also include solvates thereof. A compound represented by the formula (I) may have an asymmetric carbon atom or a double bond, and such compound may contain an optical isomer or a geometric isomer. Such isomers are also encompassed in the scope of the present invention, and can be isolated and purified according to a method known per se. Any mixture and isolated forms thereof can be used in the present invention.

In the present invention, preferable PPARα agonists from among the compounds represented by the formula (I) include 1-methyl ethyl 2-(4-(4-chlorobenzoyl)phenoxy)-2-methyl-propionate (fenofibrate; CAS registration number 49562-28-9), ((4-chloro-6-((2,3-dimethylphenyl)amino)-2-pyrimidinyl)thio)acetic acid (WY-14643; CAS registration number 50892-23-4) and the like. Preferable PPARδ agonists include 4-(3-(4-acetyl-3-hydroxy-2-propyl)phenoxy)propoxyphenoxyacetic acid (L-165041; CAS registration number 79558-09-1), (2-methyl-4-(((4-methyl-2-(4-(trifluoromethyl)phenyl)-5-thiazolyl)methyl)thio)phenoxy)acetic acid (GW-501516; CAS registration number 317318-70-0), (4-(((2-(3-fluoro-4-(trifluoromethyl)phenyl)-4-methyl-5-thiazolyl)methyl)thio)-2-methylphenoxy)acetic acid (GW-0742; CAS registration number 317318-84-6) and the like.

Preferable δ agonists include a compound represented by the following formula (II):

[Chemical formula 4]

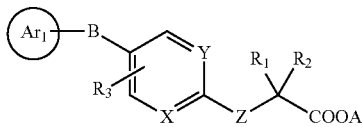

(II)

wherein
A is a hydrogen atom or an alkyl group having a carbon number of 1-6,
B is a linker selected from the group consisting of —(CH$_2$)$_n$—S— and —O—(CH$_2$)$_n$—O— wherein n is an integer of 1-3,
X and Y are the same or different and each is a carbon atom or a nitrogen atom,
Z is an oxygen atom, a sulfur atom or —CH$_2$—,
Ar$_1$ is a 5- or 6-membered aromatic ring group optionally having 1-3 substituents,
R$_1$ and R$_2$ are the same or different and each is a hydrogen atom or an alkyl group having a carbon number of 1-6, and
R$_3$ is hydrogen, a halogen atom or an alkyl group having a carbon number of 1-6,
and a pharmacologically acceptable salt thereof.

Examples of the "alkyl group having a carbon number of 1-6" for A in the above-mentioned formula (II) include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl and the like.

The linker for B in the above-mentioned formula (II) is preferably —CH$_2$—S— or —O—(CH$_2$)$_3$—O—.

Examples of the 5- or 6-membered aromatic ring group for Ar$_1$ in the above-mentioned formula (II) include phenyl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like. The aromatic ring group is preferably phenyl or thiazolyl.

Examples of the substituent Ar$_1$ may have in the above-mentioned formula (II) include a halogen atom, a hydroxy group, an alkyl group having a carbon number of 1-6, a haloalkyl group having a carbon number of 1-6, an acyl group having a carbon number of 2-7 and a phenyl group optionally having an alkyl group having a carbon number of 1-6 or a haloalkyl group having a carbon number of 1-6. The substituents are preferably a chlorine atom, a hydroxy group, a methyl group, an acetyl group, a 4-trifluoromethylphenyl group and a 3-fluoro-4-methylphenyl group.

Examples of the "alkyl group having a carbon number of 1-6" for R$_1$ or R$_2$ in the above-mentioned formula (II) include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl and the like. The alkyl group having a carbon number of 1-6 is preferably methyl.

Examples of the "halogen atom" for R$_3$ in the above-mentioned formula (II) include a fluorine atom, a chlorine atom, a bromine atom and the like. The halogen atom is preferably a chlorine atom.

Examples of the "alkyl group having a carbon number of 1-6" for R$_3$ in the above-mentioned formula (II) include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl and the like. The alkyl group having a carbon number of 1-6 is preferably methyl.

Examples of the pharmaceutically acceptable salt of a compound represented by the formula (II) include acid addition salts with mineral acids such as hydrochloric acid, hydrobromic acid, hydroiodic acid, sulfuric acid, nitric acid, phosphoric acid and the like; organic acids such as formic acid, acetic acid, propionic acid, oxalic acid, malonic acid, succinic acid, fumaric acid, maleic acid, malic acid, tartaric acid, methanesulfonic acid, ethanesulfonic acid and the like; acidic amino acids such as aspartic acid, glutamic acid, etc., and the like. These salts include solvates thereof. A compound represented by the formula (II) may have an asymmetric carbon atom or a double bond, and such compound may contain an optical isomer or a geometric isomer. Such isomers are also encompassed in the scope of the present invention, and can be isolated and purified according to a method known per se. Any mixture and isolated forms thereof can be used in the present invention.

In the present invention, preferable PPARα agonists from among the compounds represented by the formula (II) include 4-(3-(2-propyl-3-hydroxy-4-acetyl)phenoxy)propyloxyphenoxyacetic acid (L-165041; CAS registration number 79558-09-1), (2-methyl-4-(((4-methyl-2-(4-(trifluoromethyl)phenyl)-5-thiazolyl)methyl)thio)phenoxy)acetic acid (GW-501516; CAS registration number 317318-70-0), (4-(((2-(3-fluoro-4-(trifluoromethyl)phenyl)-4-methyl-5-thiazolyl)methyl)thio)-2-methylphenoxy)acetic acid (GW-0742; CAS registration number 317318-84-6) and the like.

In the promoting agent of the present invention, the content of PPARα or δ agonist is generally 0.000001-1 wt %, preferably 0.00001-1 wt %, most preferably 0.0001-0.1 wt %.

The promoting agent of the present invention can contain any career in addition to the above-mentioned active ingredient. Examples of the career include solvents (e.g., water, alcohol etc.), buffers (e.g., phosphate buffer, acetate buffer, borate buffer, carbonate buffer, citrate buffer, Tris buffer, glutamic acid, epsilon aminocaproic acid etc.), preservatives (e.g., benzalkonium chloride, benzethonium chloride, chlorhexidine gluconate, chlorobutanol, benzyl alcohol, sodium dehydroacetate, paraoxybenzoates, sodium edetate, boric acid etc.), isotonicity agents (e.g., sodium chloride, potassium chloride, glycerol, mannitol, sorbitol, boric acid, glucose, propylene glycol etc.) and the like.

The promoting agent of the present invention can be used in vivo or in vitro as a medicament or a test reagent.

When the promoting agent of the present invention is used as a test reagent, it can be utilized in various aspects as test reagents in the physiology and biochemistry field.

When used as a medicament, since the promoting agent of the present invention promotes proliferation of a meibomian gland epithelial cell, it is useful as an agent for treating a disease associated with a damage or an atrophy of a meibomian gland epithelial cell, and a disease generated by deterioration in the function of a meibomian gland epithelial cell. Examples of the disease include meibomian gland dysfunction. Further, since the meibomian gland epithelial cell secretes a lipid component in a tear fluid, and this lipid prevents a tear fluid from evaporating, and stabilizes the tear fluid layer, the therapeutic agent of the present invention is useful for a disease accompanied with lipid abnormality (reduction in the secretion amount, component change) in the tear fluid. Examples of the disease include hyperevaporative dry eye. In addition, the promoting agent of the present invention is also useful in treating dry eye, corneal ulcer, superficial punctate keratitis, corneal epithelial erosion, and the like.

In addition, since the promoting agent of the present invention promotes proliferation of a corneal epithelial cell, it is also useful as an agent for treating a disease associated with a damage (i.e. a wound or a defect) of a corneal epithelial cell. The promoting agent of the present invention is useful as an agent for treating a corneal epithelial disorder, specifically, a corneal epithelial disorder associated with an endogenous disease such as Sjogren's syndrome, Stevens-Johnsons syndrome or keratoconjunctivitis sicca (dry eye); a corneal epithelial disorder accompanied with an exogenous disease in the case of post-operation, drug use, trauma or use of contact lens; or a corneal epithelial disorder accompanied with corneal ulcer or with an ocular allergic disease associated with a corneal lesion, spring catarrh or atopic keratoconjunctivitis. The promoting agent of the present invention is also useful in treating superficial punctate keratitis and corneal epithelial erosion. Further, the promoting agent of the present invention is also useful as an agent for promoting corneal wound healing.

Further, since the promoting agent of the present invention has both a corneal epithelial cell proliferation-promoting activity and a meibomian gland epithelial cell-proliferating activity, it exhibits an effect of directly acting on a corneal tissue and an effect of improving the function of a tear fluid by working on a meibomian gland cell. As a result, the agent is highly useful particularly as a therapeutic agent for hyperevaporative dry eye.

In the therapeutic agent of the present invention, the content of the PPARα or δ agonist is usually 0.000001 to 1% by weight, preferably 0.00001 to 1% by weight, most preferably 0.0001 to 0.1% by weight.

Examples of a subject to which the promoting agent or the therapeutic agent of the present invention is administered include a mammal (e.g. human, mouse, rat, hamster, rabbit, cat, dog, cattle, sheep, monkey or the like)

The therapeutic agent of the present invention can be used in a dosage form such as eyedrops, adhesive skin patches, ointments, lotions, creams, oral preparations or the like, and can contain arbitrary carriers such as pharmaceutically acceptable carriers in addition to the aforementioned active ingredients.

In the therapeutic agent of the present invention, the administration route thereof is not particularly limited as far as the aforementioned therapeutic effect is exerted, but the therapeutic agent is preferably locally administered into eyes. Examples of a dosage form for ocular local administration include eyedrops and ocular ointments.

For example, when the therapeutic agent of the present invention is used as an eyedrop or an ocular ointment, a stabilizer (e.g. sodium hydrogen sulfite, sodium thiosulfate, sodium edetate, sodium citrate, ascorbic acid, dibutylhydroxytoluene and the like), a solubilizing agent (e.g. glycerin, propylene glycol, macrogol, polyoxyethylene hardened castor oil and the like), a suspending agent (e.g. polyvinylpyrrolidone, hydroxypropylmethylcellulose, hydroxymethylcellulose, carboxymethylcellulose sodium and the like), an emulsifier (e.g. polyvinylpyrrolidone, soybean lecithin, yolk lecithin, polyoxyethylene hardened castor oil, Polysorbate 80 and the like), a buffer (e.g. a phosphate buffer, an acetate buffer, a borate buffer, a carbonate buffer, a citrate buffer, a Tris buffer, glutamic acid, ε-aminocaproic acid and the like), a thickener (e.g. a water-soluble cellulose derivative such as methylcellulose, hydroxyethylcellulose, hydroxypropylmethylcellulose or carboxymethylcellulose, sodium chondroitin sulfate, sodium hyaluronate, a carboxyvinyl polymer, polyvinyl alcohol, polyvinylpyrrolidone, macrogol and the like), a preservative (e.g. benzalkonium chloride, benzethonium chloride, chlorhexidine gluconate, chlorobutanol, benzyl alcohol, sodium dehydroacetate, paraoxybenzoic acid esters, sodium edetate, boric acid and the like), an isotonic agent (e.g. sodium chloride, potassium chloride, glycerin, mannitol, sorbitol, boric acid, glucose, propylene glycol and the like), a pH adjusting agent (e.g. hydrochloric acid, sodium hydroxide, phosphoric acid, acetic acid and the like), a refreshing agent (e.g. l-menthol, d-camphor, d-borneol, mentha oil and the like), an ointment base (white vaseline, purified lanolin, liquid paraffin, vegetable oil (olive oil, camellia oil, peanut oil and the like) and the like) can be added as an additive. While the amount of these additives varies depending on the kind, utility and the like of the additive to be added, the additive may be added at a concentration sufficient to achieve the object thereof.

When the therapeutic agent of the present invention is formulated into eyedrops or ocular ointments, they may be produced according to the method which is usually used in the pharmacy field and, for example, can be produced based on the method described in Japanese Pharmacopoeia 14$^{th}$ edition, General Rules for Preparation, item of eyedrops and item of ocular ointments.

The present invention provides a method of promoting proliferation of a meibomian gland epithelial cell, comprising administering an effective amount of a PPARα or δ agonist to a subject in need of promotion of proliferation of a meibomian gland epithelial cell. It is desirable that the method is conducted for treating meibomian gland dysfunction.

Also, the present invention provides a method of promoting proliferation of a corneal epithelial cell, comprising administering an effective amount of a PPARα or δ agonist to a subject in need of promotion of proliferation of a corneal epithelial cell. It is desirable that the method is conducted for treating a corneal epithelial disorder.

Also, the present invention provides a method of treating hyperevaporative dry eye, including administering an effective amount of a PPARα or δ agonist to a patient suffering from hyperevaporative dry eye.

The effective amount of the PPARα or δ agonist cannot be unconditionally defined and varies depending on the kind of the compound, the age, weight and condition of the administration subject, the object of treatment and the like. When the promoting agent or the therapeutic agent of the present invention is administered to a human, for example, a solution containing the PPARα or δ agonist at a concentration of usually 0.000001 to 1% by weight, preferably 0.00001 to 1% by weight, most preferably 0.0001 to 0.1 by weight, is administered by 1 or 2 droplets for one eye per administration, i.e., about 50 to 200 μL per administration, once to 8 times a day. The amount of the PPARα or δ agonist contained in a solution having a concentration and a volume within the above ranges can be given as an example of the effective amount.

EXAMPLES

In the following, the present invention is described with reference to the following Test Examples, but the present invention is not limited by them at all.

Test Example 1

Effect of PPAR Agonist on Increase in Number of Cells Using Corneal Epithelial Cell
1. Animal Used
A male rabbit (Japanese white, KITAYAMA LABES Co., Ltd.) was used. The experimental animal was used according to the International Guiding Principles for Biomedical Research Involving Animals.
2. Preparation of Corneal Epithelial Cell
A corneal epithelial cell was prepared from rabbit eyeballs. A cornea was excised from isolated eyeballs, and stored in Dulbecco's phosphate buffered saline (D-PBS; Invitrogen), and this was transferred to a clean bench. The following cell preparation procedures were all performed sterilely.
The isolated corneal segment was washed with D-PBS with 1% penicillin-streptomycin (Invitrogen) added thereto three times, and was transferred to a minimum essential medium (MEM; Invitrogen). A corneal endothelial cell and a Descemet's membrane of the corneal segment immersed in MEM were peeled with a knife (Alcon) for ocular operation, and the corneal segment (corneal stroma and corneal epithelium) after peeling was transferred to MEM to which dispase II (Roche Diagnostics) had been added to 2.4 U/mL. This was incubated at 37° C. for 1 hour and, thereafter, the dispase II-treated corneal segment was transferred to MEM. The corneal epithelium of the corneal segment immersed in MEM was peeled with the knife for ocular operation, and the corneal segment residue (corneal stroma) was removed from MEM. The peeled corneal epithelial cell and the MEM containing same were recovered in a 50 mL centrifuge tube, subjected to centrifugation at 1,500 rpm for 5 minutes at room temperature. The supernatant was discarded to give a corneal epithelial cell layer. To the corneal epithelial cell layer was added 1 mL of trypsin-EDTA (Invitrogen) and, after thorough mixing, the cells were incubated at 37° C. for 5 minutes to dissociate adhesion between the cells. To this was added 9 mL of MEM containing 10% fetal bovine serum (FBS; Invitrogen) to stop the enzymatic reaction, and this was subjected again to centrifugation at room temperature and 1,500 rpm for 5 minutes to obtain the corneal epithelial cell layer. To the resulting corneal epithelial cell layer was added 1 mM of a serum-free liquid medium for proliferating a normal rabbit corneal epithelial cell (RCGM2; Kurabo Industries LTD.) to suspend the cell, and this was seeded into a culture dish (IWAKI) for culturing a cell having a diameter of 10 cm, to which 9 mL of RCGM2 had been added. The seeded cell was cultured in an incubator (SANYO) set at 37° C., 5% $CO_2$, 95% air, and 100% humidity. The culture medium was exchanged with a fresh culture medium every 48 hours until the test day.
3. Test Substance and Preparation Method
As the test substance, the following compounds were used.
PPARα agonist: WY-14643 (Calbiochem) and fenofibrate (Sigma-Aldrich)
PPARδ agonist: L-165041 (Sigma-Aldrich)
Each test substance was dissolved in ethanol (Wako Pure Chemical Industries, Ltd.) to a 200-fold concentration of a final concentration in the culture medium, and stored at −80° C. until immediately before use.
For studying the effect of promoting cell proliferation by each test substance, a culture medium prepared by removing a mouse-derived epithelial growth factor (mEGF) attached to RCGM2, from RCGM2, was used as a basal medium, while as a positive control for confirming the effect of promoting cell proliferation, a medium with an mEGF added thereto (basal medium+10 ng/mL mEGF) was used according to instructions of an RCGM2 preparation protocol.
4. Test Method
1) Collagen Treatment of Culture Dish
As a culture dish for a test of cell proliferation promotion, a 96-well culture dish for tissue culture (Corning) was used. On the day before the test, each 50 μL of 0.01% type I collagen (Nitta Gelatin Inc.) was dispensed into each well of the culture dish, and coating was performed at 4° C. until immediately before the test. On the test day, after a type I collagen solution was removed, the bottom of the culture dish was washed three times using D-PBS, and this was used in the test as a collagen-treated culture dish.
2) Cell Culture and Addition of Test Substance
In the test, a rabbit corneal epithelial cell which had been cultured to subconfluent in a culture dish having a diameter of 10 cm was used. After the culture medium was removed, the bottom of the culture dish was washed two times using D-PBS, to this was added 1 mL of trypsin-EDTA, this was incubated at 37° C. for 5 minutes and thereby, the cell was peeled from the bottom of the culture dish. After incubation, 9 mL of MEM containing 10% FBS was added to the culture dish to stop the enzymatic reaction, and this was subjected to centrifugation at room temperature and 1,500 rpm for 5 minutes to obtain a corneal epithelial cell layer. To the resulting cell was added an appropriate amount of RCGM2 to a cell concentration of $2 \times 10^5$ cells/mL to suspend the cell. Each 64 μL of this cell suspension was dispensed in each well at the cell number per bottom area (0.32 $cm^2$) of the collagen-treated 96-well culture dish for tissue culture of $4 \times 10^4$ cells/$cm^2$. After completion of cell seeding, the culture dish was transferred to an incubator set at 37° C., 5% $CO_2$, 95% air, and 100% humidity, and this was cultured for 24 hours. After 24 hours from cell seeding, the culture medium was discarded, and each 100 μL of the following culture media were freshly dispensed into each well of the culture dish.
[1] Only basal medium (no addition group)
[2] Basal medium+mEGF (final concentration: 10 ng/mL; positive control group)
[3] Basal medium+WY-14643 (final concentration: 0.1 μM and 1 μM)
[4] Basal medium+fenofibrate (final concentration: 1 μM and 10 μM)
[5] Basal medium+L-165041 (final concentration: 0.1 μM and 1 μM)
To equalize ethanol concentrations in all culture media to 0.5%, 5 μL/1 mL of ethanol was added to culture media [1] and [2], respectively.

3) Measurement of Cell Number

After 48 hours from culture medium exchange, the culture supernatant of each well was removed and then, each 100 μL of the basal medium with a 10% Cell Counting Kit-8 (DOJINDO) added thereto was dispensed into each well. After dispensing, the culture dish was transferred to an incubator set at 37° C., 5% $CO_2$, 95% air, and 100% humidity, and this was incubated for 2 hours. After incubation for 2 hours, the absorbance at 450 nm was measured using a microplate reader (Dainippon Pharmaceutical Co., Ltd.), and this was used as an index of an increase in the cell number.

5. Statistical Analysis

Assuming that an average of the absorbance of the no addition group was 100%, the value of each group of the no addition group, each test substance addition group and the positive control group was calculated, and comparison between the no addition group with each test substance addition group and the positive control group was performed using a Dunnett multiple comparison test method (two tail). As a result of the test, less than a significance level of 5% was determined to be significant.

6. Test Results

The effect of increasing the cell number of each group is shown in Table 1. Assuming that cell proliferation of the no addition group was 100%, cell proliferation in all of the test substance addition groups and the positive control group was significantly higher than in the no addition group ($p<0.01$) and it was shown that cell proliferation was enhanced. From this test result, it was made clear that the PPARα agonist and the PPARδ agonist increase the number of corneal epithelial cells.

TABLE 1

| Group | Cell proliferation (%) | Significant difference (to the no addition group) |
|---|---|---|
| No addition group | 100.0 ± 5.2 | |
| Positive control group (mEGF) | 144.1 ± 23.1 | ** |
| $10^{-7}$M WY-14643 | 148.9 ± 15.0 | ** |
| $10^{-6}$M WY-14643 | 155.5 ± 9.4 | ** |
| $10^{-6}$M fenofibrate | 147.3 ± 11.8 | ** |
| $10^{-5}$M fenofibrate | 147.0 ± 3.2 | ** |
| $10^{-7}$M L-165041 | 163.3 ± 8.2 | ** |
| $10^{-6}$M L-165041 | 182.2 ± 13.0 | ** |

Changes in the cell number when the PPARα agonist or the PPARδ agonist or an mEGF (positive control) was added to a cultured rabbit corneal epithelial cell are shown as values when an average of the no addition group was 100% (average ± standard deviation, N = 5).
** in the table indicates a significant difference ($p < 0.01$) as compared to the no addition group.

Test Example 2

Effect of PPARδ Agonist on Increase in Cell Number Using Corneal Epithelial Cell 1. Animal Used A male rabbit (Japanese white, weight: about 1.5 kg, KITAYAMA LABES Co., Ltd.) was used. The experimental animal was used according to the International Guiding Principles for Biomedical Research Involving Animals.

2. Preparation of Corneal Epithelial Cell

A rabbit corneal epithelial cell was prepared using the same process as that of (Test example 1).

3. Test Substance and Preparation Method

As the test substance, the following compounds were used.
PPARδ agonist: L-165041 (Sigma-Aldrich) and GW-501516 (Alexis)

Each test substance was dissolved in ethanol (Wako Pure Chemical Industries, Ltd.) to a 200-fold concentration of a final concentration in the culture media, and this was stored at −80° C. until immediately before use.

For studying the effect of promoting cell proliferation by each test substance, a culture medium prepared by removing a mouse-derived epithelial growth factor (mEGF) attached to RCGM2, from RCGM2, was used as a basal medium, while as a positive control for confirming the effect of promoting cell proliferation, a medium with an mEGF added thereto (basal medium+10 ng/mL mEGF) was used according to instructions of an RCGM2 preparation protocol.

4. Test method

1) Collagen Treatment of Culture Dish

Collagen treatment of the culture dish was performed using the same process as that of (Test Example1).

2) Cell Culture and Addition of Test Substance

In the test, a rabbit corneal epithelial cell which had been cultured to subconfluent in a culture dish having a diameter of 10 cm was used. After the culture medium was removed, the bottom of the culture dish was washed two times using D-PBS, to this was added 1 mL of trypsin-EDTA, this was incubated at 37° C. for 5 minutes and thereby, the cell was peeled from the bottom of the culture dish. After incubation, 9 mL of MEM containing 10% FBS was added to the culture dish to stop the enzymatic reaction, and this was subjected to centrifugation at room temperature and 1,500 rpm for 5 minutes to obtain a corneal epithelial cell layer. To the resulting cell was added an appropriate amount of RCGM2 to a cell concentration of $1\times10^5$ cells/mL to suspend the cell. Each 64 μL of this cell suspension was dispensed in each well at the cell number per bottom area (0.32 $cm^2$) of the collagen-treated 96-well culture dish for tissue culture of $2\times10^4$ cells/$cm^2$. After completion of cell seeding, the culture dish was transferred to an incubator set at 37° C., 5% $CO_2$, 95% air, and 100% humidity, and this was cultured for 24 hours. After 24 hours from cell seeding, the culture medium was discarded, and each 100 μL of the following culture media were freshly dispensed into each well of the culture dish.

[1] Only basal medium (no addition group)
[2] Basal medium+mEGF (final concentration: 10 ng/mL; positive control group)
[3] Basal medium+L-165041 (final concentration: 0.1 μM and 1 μM)
[4] Basal medium+GW-501516 (final concentration: 0.01 μM and 0.1 μM)

To equalize ethanol concentrations in all culture media to 0.5%, 5 μL/1 mL of ethanol was added to culture media [1] and [2], respectively.

3) Measurement of Cell Number

The culture supernatant of each well was removed every 48 hours from exchange of the culture medium containing a test substance, and each 100 μL of the freshly prepared culture medium was dispensed into each well. After 120 hours from initial exchange into a culture medium containing a test substance, the culture supernatant of each well was removed and then, each 100 μL of a basal medium with a 10% Cell Counting Kit-8 (DOJINDO) added thereto was dispensed into each well. After dispensing, the culture dish was transferred to an incubator set at 37° C., 5% $CO_2$, 95% air, and 100% humidity, and this was incubated for 2 hours. After incubation for 2 hours, the absorbance at 450 nm was measured using a microplate reader (Dainippon Pharmaceutical Co., Ltd.), and this was used as an index of an increase in the cell number.

5. Statistical Analysis

Assuming that an average of the absorbance of the no addition group was 100%, the value of each group of the no addition group, each test substance addition group and the positive control group was calculated, and comparison between the no addition group with each test substance addition group and the positive control group was performed using a Dunnett multiple comparison test method (two tail). As a result of the test, less than a significance level of 5% was determined to be significant.

6. Test Results

The effect of increasing the cell number of each group is shown in Table 2. Assuming that cell proliferation of the no addition group was 100%, cell proliferation in all of the test substance addition groups and the positive control group was significantly higher than in the no addition group (p<0.01) and it was shown that cell proliferation was enhanced. From this test result, it was made clear that the compound having a PPARδ agonist activity increases the number of corneal epithelial cells.

TABLE 2

| Group | Cell proliferation (%) | Significant difference (to the no addition group) |
| --- | --- | --- |
| No addition group | 100.0 ± 19.4 | |
| Positive control group (mEGF) | 222.1 ± 50.9 | ** |
| $10^{-7}$ M L-165041 | 242.5 ± 36.2 | ** |
| $10^{-6}$ M L-165041 | 198.6 ± 26.7 | ** |
| $10^{-8}$ M GW-501516 | 223.9 ± 24.1 | ** |
| $10^{-7}$ M GW-501516 | 213.2 ± 34.0 | ** |

Changes in the cell number when the PPARδ agonist or an mEGF (positive control) was added to a cultured rabbit corneal epithelial cell are shown as values relative to the average of the no addition group as 100% (average ± standard deviation, N = 5).
** in the table indicates a significant difference (p < 0.01) compared with the no addition group.

Test Example 3

Effect of PPAR Agonist on Increase in Cell Number Using Meibomian Gland Epithelial Cell 1. Animal Used A female cynomolgus monkey (Environmental Biological Life Science Research Center) was used. The experimental animal was used according to the International Guiding Principles for Biomedical Research Involving Animals.

2. Preparation of Meibomian Gland Epithelial Cell

A meibomian gland epithelial cell was prepared from a monkey eyelid. An eyelid was isolated, and stored in Dulbecco's phosphate buffered saline (D-PBS; Invitrogen), and this was transferred to a clean bench. The following cell preparation procedures were all performed sterilely.

After the isolated eyelid was immersed in 80% ethanol for 30 seconds, the eyelid was washed with D-PBS with 1% penicillin-streptomycin (Invitrogen) added thereto three times, and transferred to a minimum essential medium (MEM; Invitrogen). A fat tissue and a muscle tissue surrounding a meibomian gland tissue were removed under a stereomicroscope, and this was transferred to MEM containing 0.475 U/mL of collagenase A (Roche Diagnostics) and 2.4 U/mL of dispase II (Roche Diagnostics), and incubated at 37° C. overnight. After completion of incubation, the enzyme-treated tissue was placed again under the stereomicroscope, eyelashes and an eyelid connective tissue were removed, and a meibomian gland tissue was isolated. To the isolated gland tissue was added 1 mL of trypsin-EDTA (Invitrogen), and this was incubated at 37° C. for 5 minutes. After incubation, to this was added 9 mL of MEM containing 10% FBS to stop the enzymatic reaction, then, suction and exhaustion were repeated five times using a 10 mL pipette and, further, five times using an injection syringe equipped with a 21 G injection needle to disperse tissue-constituting cells. The cell dispersion was subjected to a 100 µm, then, 40 µm nylon filer (Cell Strainer; Falcon), to remove cell masses contained in the dispersion which had not been enzyme-treated. The cell suspension which had passed through the filter was recovered in a 50 mL centrifuge tube, and subjected to centrifugation at room temperature and 1,500 rpm for 5 minutes. To a cell layer containing an objective cell obtained by centrifugation was added 80 µL of D-PBS containing 0.5% bovine serum albumin (BSA; Sigma-Aldrich) to sufficiently suspend the cell, to this was added 20 µL of Anti-Fibroblast Microbeads (Militenyi Biotec), and this was allowed to stand at room temperature for 30 minutes. After completion of the reaction with an antibody, to this was added 2 mL of D-PBS containing 0.5% BSA, and this was subjected again to centrifugation at room temperature and 1,500 rpm for 5 minutes. To a cell layer containing an objective cell obtained by centrifugation was added 1 mL of D-PBS containing 0.5% BSA to sufficiently suspend the cell, and this was added dropwise to an LD column (Militenyi Biotec) equilibrated in advance using a column washing solution (D-PBS containing 2 mM EDTA (Dojindo Laboratories) and 0.5% BSA). Then, 2 mL of the column washing solution was added dropwise to the LD column. From immediately after dropwise addition of the cell suspension to completion of dropwise addition of the column washing solution, an objective cell (non-fibroblast) unlabeled with an antibody which had not been adsorbed onto the column was recovered in a 50 mL centrifuge tube. The cell recovered in the centrifuge tube was subjected again to centrifugation at room temperature and 1,500 rpm for 5 minutes to remove the supernatant. To this precipitation was added 1 mL of Defined Keratinocyte-Serum Free Medium (DK-SFM; Invitrogen) to suspend the cell and thereby, a meibomian gland epithelial cell suspension was prepared. The prepared cell was seeded on a culture dish (IWAKI) for cell culturing having a diameter of 3.5 cm which had been coated with a type I collagen solution (Nitta Gelatin Inc.) in advance, and to which 3 mL of DK-SFM had been added. The seeded cell was cultured in an incubator (SANYO) set at 37° C., 5% $CO_2$, 95% air, and 100% humidity, and the culture medium was exchanged with a fresh culture medium every 48 hours until the test day.

3. Test Substance and Preparation Method

As a test substance, the following compounds were used.
PPARα agonist: fenofibrate (Sigma-Aldrich)
PPARδ agonist: L-165041 (Sigma-Aldrich)
PPARγ agonist: troglitazone (Calbiochem)

Each test substance was dissolved in ethanol (Wako Pure Chemical Industries, Ltd.) to a 200-fold concentration of a final concentration in the culture medium, and this was stored at −80° C. until immediately before use.

For studying the effect of promoting cell proliferation by each test substance, a culture medium obtained by removing the supplement attached to DK-SFM, from DK-SFM, was used as a basal medium, while as a positive control for confirming the effect of promoting cell proliferation, a medium with the supplement added thereto (basal medium+supplement) was used according to instructions of a DK-SFM preparation protocol.

4. Test Method

1) Collagen Treatment of Culture Dish

As a culture dish for a cell proliferation promotion test, a 96-well culture dish for tissue culture (Corning) was used. On the day before the test, each 50 µL of 0.01% type I collagen (Nitta Gelatin Inc.) was dispensed into each well of the culture dish, and coating was performed at 4° C. until immediately before the test. On the test day, after a type I collagen solution was removed, the bottom of the culture dish was washed three times using D-PBS, and this was used in the test as a collagen-treated culture dish.

2) Cell Culture and Addition of Test Substance

In the test, a monkey meibomian gland epithelial cell which had been cultured to subconfluent in a culture dish having a diameter of 3.5 cm, and cryopreserved in liquid nitrogen, was used. The cell which had been suspended in a cell banker (Nippon Zenyaku Kogyo Co., Ltd.), and had been cryopreserved, was thawed, and transferred to a 50 mL centrifuge tube and a 10-fold amount of DK-SFM was added. After this was subjected to centrifugation at room temperature and 1,500 rpm for 5 minutes to recover a cell layer, an appropriate amount of DK-SFM was added to suspend the cell so that the resulting cell concentration became $3\times10^6$ cells/mL. Each 64 µL of this cell suspension was dispensed into each well so that the cell number per bottom area (0.32 cm$^2$) of the collagen-treated 96-well culture dish for tissue culture became $6\times10^4$ cells/cm$^2$. After completion of cell seeding, the culture dish was transferred to an incubator set at 37° C., 5% $CO_2$, 95% air, and 100% humidity, and this was cultured for 24 hours. After 24 hours from cell seeding, the culture medium was discarded, and each 100 µL of the following culture media were freshly dispensed into each well of the culture dish.

[1] Only basal medium (no addition group)
[2] Basal medium+supplement (positive control group)
[3] Basal medium+fenofibrate (final concentration: 1 µM and 10 µM)
[4] Basal medium+L-165041 (final concentration: 0.1 µM and 1 µM)
[5] Basal medium+troglitazone (final concentration: 0.1 µM and 1 µM)

To equalize ethanol concentrations in all culture media to 0.5%, 5 µL/1 mL of ethanol was added to culture media [1] and [2], respectively.

3) Measurement of Cell Number

After 48 hours from initial culture medium exchange, the culture medium was exchanged with the freshly prepared culture medium of each of the aforementioned [1] to [4]. Further, after 48 hours therefrom, the culture supernatant of each well was removed, then, each 100 µL of DK-SFM with a 10% Cell Counting Kit-8 (DOJINDO) added thereto was dispensed into each well. After dispensing, the culture dish was transferred to an incubator set at 37° C., 5% $CO_2$, 95% air, and 100% humidity, and this was incubated for 2 hours. After incubation for 2 hours, the absorbance at 450 nm was measured using a microplate reader (Dainippon Pharmaceutical Co., Ltd.), and this was used as an index of an increase in the cell number.

5. Statistical Analysis

Assuming that an average of the absorbance of the no addition group was 100%, the value of each group of the no addition group, each test substance addition group and the positive control group was calculated, and comparison between the no addition group with each test substance addition group and the positive control group was performed using a Dunnett multiple comparison test method (two tail). As a result of the test, less than a significance level of 5% was determined to be significant.

6. Test Results

The effect of increasing the cell number of each group is shown in Table 3. Assuming that cell proliferation of the no addition group was 100%, cell proliferation in an addition group of fenofibrate which is a PPARα agonist and an addition group of L-165041 which is a PPARδ agonist, and the positive control group was significantly higher than in the no addition group (p<0.01) and it was shown that cell proliferation was enhanced. On the other hand, troglitazone, which is a PPARγ agonist, showed no cell proliferation promoting activity. From this test result, it was made clear that the PPARα agonist and the PPARδ agonist increase the number of meibomian gland epithelial cells.

TABLE 3

| Group | Cell proliferation (%) | Significant difference (to the no addition group) |
|---|---|---|
| No addition group | 100.0 ± 4.7 | |
| Positive control group (supplement) | 131.4 ± 5.7 | ** |
| $10^{-6}$ M fenofibrate | 114.5 ± 4.5 | ** |
| $10^{-5}$ M fenofibrate | 127.8 ± 5.2 | ** |
| $10^{-7}$ M L-165041 | 136.1 ± 4.7 | ** |
| $10^{-6}$ M L-165041 | 142.8 ± 5.4 | ** |
| $10^{-7}$ M troglitazone | 101.6 ± 4.0 | |
| $10^{-6}$ M troglitazone | 99.9 ± 1.9 | |

Changes in the cell number when the PPARα agonist, the PPARδ agonist or the PPARγ agonist or the supplement (positive control) was added to a cultured monkey meibomian gland epithelial cell are shown as values when an average of the no addition group was 100% (average ± standard deviation, N = 5).
** in the table indicates a significant difference (p < 0.01) as compared to the no addition group.

Test Example 4

Expression of PPARs in Corneal Epithelial Cell and Meibomian Gland Epithelial Cell 1. Cell Used As a rabbit corneal epithelial cell, a cell prepared and cultured by the same process as that of (Test Example 1) was used. As a monkey meibomian gland epithelial cell, a cell prepared and cultured by the same process as that of (Test Example 3) was used. As a human corneal epithelial cell (Kurabo Industries LTD.), a cell cultured in an incubator set at 37° C., 5% $CO_2$, 95% air, and 100% humidity using a serum-free basal medium (EpiLife; Kurabo Industries LTD.) for proliferating a normal human corneal epithelial cell, was used.

2. Test Method

1) Extraction of Total RNA from Cell

A total RNA was extracted from each cell according to a conventional method of TRizol Reagent (Invitrogen).

2) Preparation of cDNA from Extracted RNA

DNase treatment of a total RNA extracted according to a DNA-free (Ambion) conventional method was performed at 37° C. for 30 minutes, to remove a genome DNA.

Preparation of a cDNA from the extracted RNA was performed according to a conventional method of Superscript II Reverse Transcriptase (Invitrogen). That is, using random primers (Invitrogen), a cDNA complementary therewith was prepared from 1 µg of a DNase-treated total RNA.

3) Amplification of PPARs Genes (Polymerase Chain Reaction; PCR)

PCR of PPARs genes was performed according to a conventional method of Platinum PCR SuperMix (Invitrogen). PPARs primers were designed so that the PCR product became about 200 bps, referring to the known sequences of a human, a chimpanzee, a cynomolgus monkey, cattle, and a mouse.

PPARα:

GTAGAATCTGCGGGGACAAG (SEQ ID No.: 1)
(sense)

: GTTGTGTGACATCCCGACAG (SEQ ID No.: 2)
(antisense)

PPARδ:

TTCCTTCCAGCAGCTACACA (SEQ ID No.: 3)
(sense)

: GATCGTACGACGGAAGAAGC (SEQ ID No.: 4)
(antisense)

PPARγ:

CTCCGTGGATCTCTCCGTAA (SEQ ID No.: 5)
(sense)

: GATGCAGGCTCCACTTTGAT (SEQ ID No.: 6)
(antisense)

The PCR reaction was completed by repeating a three-stage reaction of at 94° C. for 30 seconds, at 55° C. for 30 seconds, and at 72° C. for 30 minutes thirty five times, after a reaction at 94° C. for 2 minutes and 15 seconds. A sample after the PCR reaction was subjected to electrophoresis using a 2% agarose gel and then, a DNA separated in the gel was stained using SYBR Gold (Molecular Probes). The stained DNA was made to emit light on a UV transilluminator, and this image was stored as digital data.

3. Test Results

A band of the stained DNA after electrophoresis is shown in FIG. 1. As a result of this test, it was confirmed that all of PPARα, PPARδ and PPARγ are expressed in a human corneal epithelial cell and a monkey meibomian gland epithelial cell. In addition, in a rabbit corneal epithelial cell, expression of only PPARδ was confirmed. Bonazzi et al. report that, among PPARs, PPARα and PPARβ (=δ) are expressed in a rabbit corneal epithelial cell (Bonazzi A. et al., J. Biol. Chem. (2000); 275 (4): 2837-2844) and in their report, they use a special method for detecting PPARα. As shown in Test Example 1, it is clear that PPARα agonist promotes proliferation of a rabbit corneal epithelial cell, and since in the report by Bonazzi et al., PPARα is detected using the special detection method, it is suggested that an expression amount of a PPARα in a rabbit corneal epithelial cell is very small.

Test Example 5)

Effect of PPARδ Agonist on Increase in Number of Cells Using Normal Human Corneal Epithelial Cell 1. Cell Used A normal human corneal epithelial cell (KURABO) was used.

2. Test Substance and Preparation Method

As the test substance, the following compounds were used. PPARδ agonist: L-165041 (Sigma-Aldrich), GW-501516 (Alexis)

Each test substance was dissolved in ethanol (Wako Pure Chemical Industries, Ltd.) to a 200-fold concentration of a final concentration in the culture medium, and stored at −80° C. until immediately before use.

For studying the effect of promoting cell proliferation by each test substance, as a cell culture medium, medium (basal medium) in which insulin, hydrocortisone, and transferrin contained in an HCGS proliferation additive set (KURABO) were added to EpiLife (KURABO) was used. In addition, as a positive control for confirming the cell proliferation promoting effect, a medium in which a mouse-derived epithelial growth factor (mEGF) contained in an HCGS proliferation additive set (KURABO) was added to a basal medium (basal medium+1 ng/mL mEGF) was used.

3. Test Method

1) Cell Culture and Addition of Test Substance

A normal human corneal epithelial cell which had been cryopreserved in liquid nitrogen was thawed, the cell number was counted, and a total amount thereof was transferred to 4 mL of EpiLife (complete medium) with all of an HCGS proliferation additive set (insulin, mouse-derived epithelial growth factor, hydrocortisone, transferrin, bovine pituitary gland extract) added thereto to suspend them sufficiently. This cell suspension was seeded on a fibronectin-coated multiwell plate (24 well, BECTON DICKINSON) so that the cell number became $2 \times 10^4$ cells/500 μL/well (since the bottom area is 2 cm$^2$, the number is $1 \times 10^4$ cells/cm$^2$).

After completion of cell seeding, the culture dish was cultured in an incubator set at 37° C., 5% $CO_2$, 95% air, and 100% humidity for 24 hours and then, the culture medium was exchanged with each 400 μL of abased medium. Further, 24 hours thereafter, the culture medium was exchanged with each 400 μL of the following culture media.

[1] Only basal medium (no addition group)
[2] Basal medium+mEGF (final concentration: 1 ng/mL; positive control group)
[3] Basal medium+L-165041 (final concentration: 0.01 μM and 0.1 μM)
[4] Basal medium+GW-501516 (final concentration: 0.001 μM and 0.01 μM)

To equalize all ethanol concentrations in all culture media to 0.5%, each 5 μL/1 mL of ethanol was added to culture media [1] and [2], respectively.

2) Measurement of Cell Number

After 24 hours from initiation of stimulation with a test substance, the culture supernatant of each well was removed and then, each 200 μL of a basal medium with a 10% Cell Counting Kit-8 (DOJINDO) added thereto was dispensed into each well. After dispensing, the culture dish was transferred to an incubator set at 37° C., 5% $CO_2$, 95% air, and 100% humidity, this was incubated for 2 hours, and each 100 μL was taken from the supernatant after completion of the reaction into a 96-well culture dish for tissue culture (Corning). The absorbance at 450 nm of the reaction solution which had been transferred to the 96-well culture dish was measured using a microplate reader (Dainippon Sumitomo Pharmaceutical Co., Ltd.), and this was used as an index of an increase in the cell number.

4. Statistical Analysis

Assuming that an average of the absorbance of the no addition group was 100%, the value of each group of the no addition group, each test substance addition group and the positive control group was calculated, and comparison between the no addition group with each test substance addition group and the positive control group was performed using a Dunnett multiple comparison test method (one tail). As a result of the test, less than a significance level of 5% was determined to be significant.

5. Test Results

The cell number increasing effect of each group is shown in Table 4. Assuming that cell proliferation of the no addition group was 100%, cell proliferation in the test substance addition group (<0.01) and the positive control group (p<0.05) was significantly higher than in the no addition group and it was shown that cell proliferation was enhanced. From this test result, it was made clear that the PPARδ agonist increases the number of a normal human corneal epithelial cell.

TABLE 4

| Group | Cell proliferation (%) | Significant difference (to the no addition group) |
|---|---|---|
| No addition group | 100.0 ± 7.9 | |
| Positive control group (mEGF) | 112.1 ± 1.5 | * |
| $10^{-8}$ M L-165041 | 128.1 ± 5.3 | ** |
| $10^{-7}$ M L-165041 | 127.8 ± 6.0 | ** |
| $10^{-9}$ M GW-501516 | 133.1 ± 3.7 | ** |
| $10^{-8}$ M GW-501516 | 125.7 ± 2.3 | ** |

Changes in the cell number when the PPARδ agonist or the mEGF (positive control) was added to a cultured normal human corneal epithelial cell are shown as values relative to the average of the no addition group as 100% (average ± standard deviation, N = 3 to 4).
* in the table indicates a significant difference compared with the no addition group (<0.05), and
** in the table indicates a significant difference as compared to the no addition group (p < 0.01).

Test Example 6

Effect of PPARδ Agonist on Increase in Cell Number Using Normal Human Corneal Epithelial Cell
1. Cell Used
A normal human corneal epithelial cell (KURABO) was used.
2. Test Substance and Preparation Method
As the test substance, the following compounds were used.
PPARδ Agonist: GW-501516 (Alexis), GW-0742 (Sigma-Aldrich)
Each test substance was dissolved in ethanol (Wako Pure Chemical Industries, Ltd.) to a 200-fold concentration of a final concentration in the culture medium, and stored at −80° C. until immediately before use.
For studying the effect of promoting cell proliferation by each test substance, as a cell culture medium, a medium (basal medium) in which insulin, hydrocortisone, and transferrin contained in an HCGS proliferation additive set (KURABO) were added to EpiLife (KURABO) was used.
3. Test Method
1) Cell Culture and Addition of Test Substance
A normal human corneal epithelial cell which had been cryopreserved in liquid nitrogen was thawed, the cell number was counted, and a total amount thereof was transferred to 4 mL of EpiLife (complete medium) with all of an HCGS proliferation additive set (insulin, mouse-derived epithelial growth factor, hydrocortisone, transferrin, bovine pituitary gland extract) added thereto to suspend them sufficiently. This cell suspension was seeded on a 96-well culture dish for tissue culture (Corning) so that the cell number became 1.28× $10^4$ cells/100 µL/well (since the bottom area is 0.32 cm$^2$, the number is 4×$10^4$ cells/cm$^2$).

After completion of cell seeding, the culture dish was cultured in an incubator set at 37° C., 5% CO$_2$, 95% air, and 100% humidity for 24 hours and then, the culture medium was exchanged with 100 µL of a basal medium (EpiLife to which insulin, hydrocortisone, and transferrin of an HCGS proliferation additive were added).

Further, 24 hours thereafter, the culture medium was exchanged with each 100 µL of the following culture media.
[1] Only basal medium (no addition group)
[2] Basal medium+GW-501516 (final concentration: 0.01 µM)
[3] Basal medium+GW-0742 (final concentration: 0.01 µM)

To equalize all ethanol concentrations in all culture media to 0.5%, 5 µL/1 mL of ethanol was added to the culture medium [1].
2) Measurement of Cell Number
After 48 hours from initiation of stimulation with a test substance, the culture supernatant of each well was removed and then, each 100 µL of a basal medium with a 10% Cell Counting Kit-8 (DOJINDO) added thereto was dispensed into each well. After dispensing, the culture dish was transferred to an incubator set at 37° C., 5% CO$_2$, 95% air, and 100% humidity, and this was incubated for 2 hours. The absorbance at 450 nm of each well was measured using a microplate reader (Dainippon Sumitomo Pharmaceutical Co., Ltd.), and this was used as an index of an increase in the cell number.
4. Statistical Analysis
Assuming that an average of the absorbance of the no addition group was 100%, the value of the no addition group, and each test substance addition group was calculated, and comparison between the no addition group with each test substance addition group and the positive control group was performed using a Dunnett multiple comparison test method (one tail). As a result of the test, less than a significance level of 5% was determined to be significant.
5. Test Results
The cell number increasing effect of each group is shown in Table 5. Assuming that proliferation of the no addition group was 100%, cell proliferation in the both test substance addition groups was significantly higher than in the no addition group and it was shown that cell proliferation was enhanced (p<0.01). From this test result, it was made clear that the PPARδ agonist increases the number of a normal human corneal epithelial cell.

TABLE 5

| Group | Cell proliferation (%) | Significant difference (to the no addition group) |
|---|---|---|
| No addition group | 100.0 ± 8.3 | |
| $10^{-8}$ M GW-501516 | 129.2 ± 7.5 | ** |
| $10^{-8}$ M GW-0742 | 124.1 ± 13.5 | ** |

Changes in the cell number when the PPARδ agonist was added to a cultured normal human corneal epithelial cell are shown as values relative to the average of the no addition group as 100% (average ± standard deviation, N = 4 to 5).
** in the table indicates a significant difference as compared to the no addition group (p < 0.01).

Test Example 7

Effect of PPARγ Agonist on Increase in Cell Number Using Normal Human Corneal Epithelial Cell
1. Cell Used
A normal human corneal epithelial cell (KURABO) was used.
2. Test Substance and Preparation Method
As the test substance, the following compound was used.
PPARγ agonist: troglitazone (Calbiochem)
The test substance was dissolved in ethanol (Wako Pure Chemical Industries, Ltd.) to a 200-fold concentration of a final concentration in the culture medium, and stored at −80° C. until immediately before use.
For studying the influence of each test substance on a normal human corneal epithelial cell, as a cell culture medium, a medium (EpiLife basal medium) in which insulin, hydrocortisone, and transferrin except for a mouse-derived epithelial growth factor (mEGF) of additives contained in an HCGS proliferation additive set (KURABO) were added to EpiLife (KURABO) was used.

3. Test Method

1) Cell Culture and Addition of Test Substance

Normal Human Corneal Epithelial Cell

A normal human corneal epithelial cell which had been cryopreserved in liquid nitrogen was thawed, the cell number was counted, and a total amount thereof was transferred to EpiLife (complete medium) with all of an HCGS proliferation additive set containing an mEGF added thereto to suspend them sufficiently. This cell suspension was seeded on a multiwell plate which had been collagen-coated as in Test Example 1 (96-well, Costar) so that the cell number became $1.28 \times 10^4$ cells/64 μL/well (since the bottom area is 0.32 cm$^2$, the number is $4 \times 10^4$ cells/cm$^2$).

After completion of cell seeding, the culture dish was cultured in an incubator set at 37° C., 5% $CO_2$, 95% air, and 100% humidity for 24 hours and then, the culture medium was exchanged with each 100 μL of the culture media containing the following test substance, and the culture was continued.

[1] Only EpiLife basal medium (no addition group)
[2] EpiLife basal medium+troglitazone (final concentration: 0.1 μM)

To equalize all ethanol concentrations in all culture media to 0.5%, 5 μL/1 mL of ethanol was added to culture medium [1]. Between the test substance addition initiation day and the cell number measuring day, the culture medium was exchanged with a culture medium containing the aforementioned test substance every 2 days.

2) Measurement of Cell Number

After 6 days from initiation of stimulation with a test substance, the culture supernatant of each well was removed and, then, each 100 μL of an EpiLife basal medium with a 10% Cell Counting Kit-8 (DOJINDO) added thereto was dispensed into each well. After dispensing, the culture dish was transferred to an incubator set at 37° C., 5% $CO_2$, 95% air, and 100% humidity, this was incubated for 2 hours, and the absorbance (450 nm) of each well of the culture dish after completion of the reaction was measured using a microplate reader (Dainippon Sumitomo Pharmaceutical Co., Ltd.), and this was used as an index of an increase in the cell number.

4. Statistical Analysis

Assuming that an average of the absorbance of the no addition group was 100%, the value of the no addition group, and each test substance addition group was calculated, and comparison between the no addition group with each test substance addition group was performed using a Dunnett multiple comparison test method (one tail). As a result of the test, less than a significance level of 5% was determined to be significant.

5. Test Results

The influence of the PPARγ agonist on a normal human corneal epithelial cell is shown in Table 6. From this test result, the effect of increasing the number of corneal epithelial cells was not recognized in the PPARγ agonist.

TABLE 6

| Group | Cell proliferation (%) |
| --- | --- |
| No addition group | 100.0 ± 6.6 |
| $10^{-7}$ M troglitazone | 74.1 ± 5.1 |

Changes in the cell number when the PPARγ agonist was added to a cultured normal human corneal epithelial cell are shown as values relative to the average of the no addition group as 100% (average±standard deviation, N=3 to 4). ** in the table indicates a significant difference as compared to the no addition group (p<0.01).

Test Example 8

Effect of PPARδ Agonist on Increase in Number of Meibomian Gland Epithelial Cells 1. Preparation of Monkey Meibomian Gland Epithelial Cell Preparation of a meibomian gland epithelial cell from a monkey eyelid was performed as in Test Example 3. The cell was cultured in an incubator (SANYO) set at 37° C., 5% $CO_2$, 95% air, and 100% humidity using a Defined keratinocyte-Serum Free Medium (DK-SFM; Invitrogen, the attached supplement was added according to the preparation protocol), and the culture medium was exchanged with a fresh one every 48 hours until the cell reached subconfluent.

2. Test Substance and Preparation Method

As the test substance, the following compounds were used.
PPARδ agonist: L-165041 (Sigma-Aldrich) and GW-501516 (Alexis)

Each test substance was dissolved in ethanol (Nacalai Tesque, Inc.) to a 200-fold concentration of a final concentration in the culture medium, and stored at −80° C. until immediately before use.

For studying the effect of promoting cell proliferation by each test substance, a culture medium prepared by removing the supplement attached to DK-SFM, from DK-SFM, was used as a basal medium, while as a positive control for confirming the cell proliferation promoting effect, a culture medium with the supplement added thereto (basal medium+supplement) was used according to instructions of an DK-SFM preparation protocol.

3. Test Method

1) Collagen Treatment of Culture Dish

A culture dish for a cell proliferation promotion test was coated using type I collagen (Nitta Gelatin Inc.) as in Test Example 3.

2) Cell Culture and Addition of Test Substance

In the test, a monkey meibomian gland epithelial cell which had been cultured to subconfluent, suspended in a cell banker (Nippon Zenyaku Kogyo Co., Ltd.), and cryopreserved in liquid nitrogen was used. The cell which had been cryopreserved was thawed, and transferred to a 50 mL centrifuge tube and a 10-fold amount of DK-SFM was added thereto. After this was subjected to centrifugation at room temperature and 1,500 rpm for 5 minutes to recover a cell layer, an appropriate amount of DK-SFM was added to suspend the cell so that the resulting cell concentration became $2 \times 10^6$ cells/mL. Each 64 μL of this cell suspension was dispensed into each well so that the cell number per bottom area (0.32 cm$^2$) of the collagen-treated 96-well culture dish for tissue culture became $4 \times 10^4$ cells/cm$^2$. After completion of cell seeding, the culture dish was transferred to an incubator set at 37° C., 5% $CO_2$, 95% air, and 100% humidity, and this was cultured for 24 hours. After 24 hours from cell seeding, the culture medium was discarded, and each 100 μL of the following culture media were freshly dispensed into each well of the culture dish.

[1] Only basal medium (no addition group)
[2] Basal medium+supplement (positive control group)
[3] Basal medium+L-165041 (final concentration: 0.1 μM and 1 μM)
[4] Basal medium+GW-501516 (final concentration: 0.01 μM and 0.1 μM)

To equalize ethanol concentrations in all culture media to 0.5%, 5 μL/1 mL of ethanol was added to culture media [1] and [2], respectively.

3) Measurement of Cell Number

After 48 hours from initial culture medium exchange, the culture medium was exchanged with a freshly prepared culture medium of each of [1] to [4]. Further, after 48 hours therefrom, the culture medium was exchanged again with a freshly prepared culture medium of each of [1] to [4]. Further, after 48 hours therefrom, the culture supernatant of each well was removed, then, each 100 μL of a basal medium with a 10% Cell Counting Kit-8 (DOJINDO) added thereto was dispensed into each well. After dispensing, the culture dish was transferred to an incubator set at 37° C., 5% $CO_2$, 95% air, and 100% humidity, and this was incubated for 2 hours. After incubation for 2 hours, the absorbance at 450 nm was measured using a microplate reader (Dainippon Pharmaceutical Co., Ltd.), and this was used as an index of an increase in the cell number.

4. Statistical Analysis

Assuming that an average of the absorbance of the no addition group was 100%, the value of each group of the no addition group, each test substance addition group and the positive control group was calculated, and comparison between the no addition group with each test substance addition group and the positive control group was performed using a Dunnett multiple comparison test method (one tail). As a result of the test, less than a significance level of 5% was determined to be significant.

5. Test Results

The effect of promoting cell proliferation of each group is shown in Table 7. Assuming that cell proliferation of the no addition group was 100%, cell proliferation in an addition group of L-165041 ($10^{-6}$ M) which is a PPARδ agonist and an addition group of GW-501516 ($10^{-7}$ M) which is also a PPARδ agonist, and the positive control group was significantly higher than in the no addition group and it was shown that cell proliferation was enhanced. From this test result, it was made clear that the PPARδ agonist increases the number of meibomian gland epithelial cells.

TABLE 7

| Group | Cell proliferation (%) | Significant difference (to the no addition group) |
|---|---|---|
| No addition group | 100.0 ± 23.9 | |
| Supplement | 149.6 ± 57.7 | * |
| $10^{-7}$ M L-165041 | 142.9 ± 22.3 | |
| $10^{-6}$ M L-165041 | 169.1 ± 19.6 | ** |
| $10^{-8}$ M GW-501516 | 133.3 ± 7.4 | |
| $10^{-7}$ M GW-501516 | 156.1 ± 18.9 | * |

Change in the cell number when the PPARδ/β agonist, or the supplement (positive control) was added to a cultured monkey meibomian gland epithelial cell are shown as values relative to the average of the no addition group as 100% (average ± standard deviation, N = 5).
* in the table indicates a significant difference as compared to the no addition group ($p < 0.05$), and
** in the table indicates a significant difference as compared to the no addition group ($p < 0.01$).

Test Example 9

Study of Healing Promoting Activity to Corneal Epithelial Wound by PPARδ Agonist 1. Animal Used A male rabbit (Japanese white, KITAYAMA LABES Co., Ltd.) was used. The experimental animal was used according to the International Guiding Principles for Biomedical Research Involving Animals.

2. Test Substance and Method of Preparing Eyedrop Solution

As the test substance, a PPARδ agonist GW-501516 (Alexis Biochemicals) was used. A solution in which GW-501516 was suspended in the following vehicle to 0.05% was used as an eyedrop solution.

| | |
|---|---|
| Sodium dihydrogen phosphate dehydrate | 0.05 g |
| Sodium chloride | 0.45 g |
| Ultrapure water | q.s. |
| Polysorbate 80 | 0.05 mL |
| NaOH | q.s. |
| Total amount | 50 mL (pH 7.0) |

As a control for the test substance administration group, the aforementioned vehicle administration group containing no drug was set.

3. Experimental Method

1) Corneal Epithelial Scraping

After the animal was subjected to systemic anesthesia by intramuscular injection (0.9 mL/kg) with a selactar (2% xylazine: Bayer): ketalar (5% ketamine: Sankyo)=0.5:1 mixed solution, an oxybuprocaine hydrochloride eyedrop solution (Benoxil eyedrop solution 0.4%; Santen Pharmaceutical Co., Ltd.) was administered, and eyeballs were exposed. A mark having a diameter of 6 mm was stamped on a corneal epithelium at a corneal central part using a trephine having a diameter of 6 mm, and a whole corneal epithelial layer within a stamped circumference was scraped using a handy rooter under a stereomicroscope. After scraping, a corneal surface was washed using physiological saline (Otsuka Pharmaceutical Factory Inc.), and eyeballs were returned into the orbit to complete the corneal epithelial scraping treatment.

2) Administration

A test substance eyedrop solution or an eyedrop solution vehicle was administered to treated eyes at 50 μL per once using a micropipette two times a day on the corneal epithelium scraping day and, on the following day and thereafter, four times a day until completion of the test.

3) Assessment

At the time point at which corneal epithelium scraping of both eyes of all individuals was completed was defined as the test initiation time (0 hour) and, by quantitating the corneal epithelial defect area at 24, 38 and 48 hours thereafter, restoration of a corneal epithelium was assessed. That is, at each time point, 10 μL of a 0.1% fluorescein sodium (Wako Pure Chemical Industries, Ltd.) solution was administered to treated eyes, a photograph of an anterior ocular segment of the animal was immediately taken using a slit lamp equipped with a cobalt filter and thereby, a stained corneal epithelial defect region was recorded. A developed photograph was stored as a digital image in a computer, and an area of the stained corneal epithelial defect part was measured using image analysis software (Image-Pro Plus).

4. Statistical Analysis

Regarding the corneal epithelial defect area measured at each time point, a value for each individual was calculated, assuming that its initial value was 100%, and this was adopted as a ratio of the remaining corneal epithelial defect. Regarding the ratio of the remaining corneal epithelial defect at each time point, comparison between the vehicle administration group and the test substance administration group was performed by a t-test, and less than a significance level of 5% was determined to be significant.

5. Test Results

The ratio of the remaining corneal epithelial defect at each time point of measurement of the vehicle administration group and the 0.05% GW-501516 administration group is shown in Table 8. It was shown that the ratio of the corneal epithelial defect was significantly decreased in the 0.05% GW-501516 administration group 24 hours and 38 hours after corneal epithelium scraping. After 48 hours, the corneal epithelial defect disappeared in all individuals. From this test result, it was made clear that restoration of the defective corneal epithelium is promoted by administration of the PPARδ agonist to eyes.

TABLE 8

| Group | Base administration group (%) | 0.05% GW-501516 administration group (%) |
|---|---|---|
| 0 hour (initial value) | 100.0 ± 4.9 | 100.0 ± 6.5 |
| 24 hours later | 33.6 ± 3.8 | 25.3 ± 3.1 * |
| 38 hours later | 3.6 ± 1.2 | 0.2 ± 0.2 ** |

A value obtained by calculating a ratio (%) of a corneal epithelial defect remaining after the corneal epithelium scraping treatment of rabbit eyes, for each individual, assuming that an initial value was 100% is shown (average ± standard deviation, N = 4).
* in the table indicates a significant difference as compared to the vehicle administration group ($p < 0.05$) and
** indicates a significant difference as compared to the vehicle administration group ($p < 0.01$).

Industrial Applicability

According to the present invention, a novel agent for promoting proliferation of a meibomian gland epithelial cell or a novel agent for promoting proliferation of a corneal epithelial cell is provided, and the promoting agent promotes proliferation of a meibomian gland epithelial cell and a corneal epithelial cell. In addition, the therapeutic agent of the present invention can be effectively used in treating/improving a disease such as meibomian gland dysfunction, corneal epithelial disorder, or hyperevaporative dry eye.

The present invention is based on Japanese patent application No. 2005-342025 filed on Nov. 28, 2005, the contents of which are hereby incorporated in full by reference.

---

The invention claimed is:

1. A method of promoting proliferation of a meibomian gland epithelial cell, comprising administering an effective amount of a peroxisome proliferator activated receptor δ (PPARδ) agonist to a subject in need of the treatment of meibomian gland dysfunction, wherein the PPARδ agonist is a compound represented by the formula (II):

[Chemical formula 2]

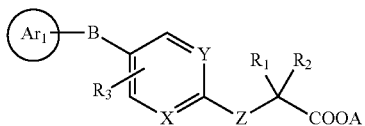

(II)

wherein

A is a hydrogen atom or an alkyl group having a carbon number of 1 to 6,

B is a linker selected from the group consisting of —(CH$_2$)$_n$—S— and —O—(CH$_2$)$_n$—O— wherein n is an integer of 1 to 3, each of X and Y is a carbon atom, Z is an oxygen atom, a sulfur atom or —CH$_2$—, Ar$_1$ is a 5- to 6-membered aromatic cyclic group optionally having 1 to 3 substituents wherein the 5- to 6-membered aromatic cyclic group is selected from a group consisting of phenyl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, R$_1$ and R$_2$ are the same or different, and each is a hydrogen atom or an alkyl group having a carbon number of 1 to 6, and R$_3$ is hydrogen, a halogen atom or an alkyl group having a carbon number of 1 to 6, or a pharmacologically acceptable salt thereof.

2. A method of treating evaporative dry eye, comprising administering an effective amount of a peroxisome proliferator activated receptor δ (PPARδ) agonist to a patient suffering from evaporative dry eye, wherein the PPARδ agonist is a compound represented by the formula (II):

[Chemical formula 2]

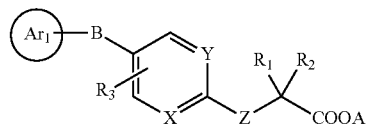

(II)

wherein

A is a hydrogen atom or an alkyl group having a carbon number of 1 to 6,

B is a linker selected from the group consisting of —(CH$_2$)$_n$—S— and —O—(CH$_2$)$_n$—O— wherein n is an integer of 1 to 3, each of X and Y is a carbon atom, Z is an oxygen atom, a sulfur atom or —CH$_2$—, Ar$_1$ is a 5- to 6-membered aromatic cyclic group optionally having 1 to 3 substituents wherein the 5- to 6-membered aromatic cyclic group is selected from a group consisting of phenyl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, R$_1$ and R$_2$ are the same or different, and each is a hydrogen atom or an alkyl group having a carbon number of 1 to 6, and R$_3$ is hydrogen, a halogen atom or an alkyl group having a carbon number of 1 to 6, or a pharmacologically acceptable salt thereof.

3. The method of claim 1, wherein the PPARδ agonist is (4-(3-(4-acetyl-3-hydroxy-2-propyl)phenoxy)propoxyphenoxy)acetic acid, (2-methyl-4-(((4-methyl-2-(4-(trifluoromethyl)phenyl)-5-thiazolyl)methyl)thio)phenoxy)acetic acid or (4-(((2-(3-fluoro-(4-(trifluoromethyl)phenyl)-4-methyl-5-thiazolyl)methyl)thio)-2-methylphenoxy)acetic acid, or a pharmacologically acceptable salt thereof.

4. The method of claim 2, wherein the PPARδ agonist is (4-(3-(4-acetyl-3-hydroxy-2-propyl)phenoxy)propoxyphenoxy)acetic acid, (2-methyl-4-(((4-methyl-2-(4-(trifluoromethyl)phenyl)-5-thiazolyl)methyl)thio)phenoxy)acetic acid or (4-(((2-(3-fluoro-(4-(trifluoromethyl)phenyl)-4-methyl-5-thiazolyl)methyl)thio)-2-methylphenoxy)acetic acid, or a pharmacologically acceptable salt thereof.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 1
gtagaatctg cggggacaag                                                  20

<210> SEQ ID NO 2
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 2
gttgtgtgac atcccgacag                                                  20

<210> SEQ ID NO 3
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 3
ttccttccag cagctacaca                                                  20

<210> SEQ ID NO 4
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 4
gatcgtacga cggaagaagc                                                  20

<210> SEQ ID NO 5
<211> LENGTH: 20
<212> TYPE: DNA
<213> ORGANISM: Artificial sequence

```
<220> FEATURE:
<223> OTHER INFORMATION: Synthetic construct; primer

<400> SEQUENCE: 5
ctccgtggat ctctccgtaa                                             20

<210> SEQ ID NO 6
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 6
gatgcaggct ccactttgat                                             20
```